(12) United States Patent
Siskin et al.

(10) Patent No.: US 8,480,795 B2
(45) Date of Patent: Jul. 9, 2013

(54) ABSORBENT COMPOSITION CONTAINING MOLECULES WITH A HINDERED AMINE AND A METAL SULFONATE, PHOSPHONATE OR CARBOXYLATE STRUCTURE FOR ACID GAS SCRUBBING PROCESS

(75) Inventors: Michael Siskin, Westfield, NJ (US); Alan R. Katritzky, Gainesville, FL (US); Frank C Wang, Annandale, NJ (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 552 days.

(21) Appl. No.: 11/989,154

(22) PCT Filed: Aug. 1, 2006

(86) PCT No.: PCT/US2006/029894
§ 371 (c)(1),
(2), (4) Date: Aug. 3, 2009

(87) PCT Pub. No.: WO2007/021531
PCT Pub. Date: Feb. 22, 2007

(65) Prior Publication Data
US 2009/0308248 A1    Dec. 17, 2009

Related U.S. Application Data

(60) Provisional application No. 60/706,615, filed on Aug. 9, 2005.

(51) Int. Cl.
*B01D 53/14*    (2006.01)
(52) U.S. Cl.
USPC .......................................................... 95/235
(58) Field of Classification Search
USPC .... 95/236, 44, 49, 51; 562/104, 512; 558/166
See application file for complete search history.

(56) References Cited

U.S. PATENT DOCUMENTS

| | | | | |
|---|---|---|---|---|
| 1,990,217 | A | * | 2/1935 | Baehr et al. .................... 423/226 |
| 2,176,441 | A | * | 10/1939 | Ulrich et al. ................... 423/228 |
| 3,042,483 | A | * | 7/1962 | Wolfram et al. ............ 423/437.1 |
| 3,532,637 | A | * | 10/1970 | Zeff et al. ...................... 252/190 |
| 3,574,551 | A | * | 4/1971 | Noll et al. ...................... 436/103 |
| 3,660,016 | A | * | 5/1972 | John et al. ...................... 423/226 |
| 4,112,051 | A | | 9/1978 | Sartori et al. |
| 4,112,052 | A | | 9/1978 | Sartori et al. |
| 4,217,238 | A | | 8/1980 | Sartori et al. |
| 4,376,101 | A | | 3/1983 | Sartori et al. |
| 4,376,102 | A | | 3/1983 | Thaler et al. |
| 4,405,579 | A | * | 9/1983 | Sartori et al. .................. 423/223 |
| 4,405,581 | A | | 9/1983 | Savage et al. |
| 4,405,585 | A | | 9/1983 | Sartori et al. |
| 4,525,294 | A | | 6/1985 | Sartori et al. |
| 4,581,209 | A | * | 4/1986 | Oswald et al. ................ 423/223 |
| 4,618,481 | A | | 10/1986 | Heinzelmann et al. |
| 4,759,866 | A | * | 7/1988 | Shulik et al. .................. 252/192 |
| 4,873,272 | A | | 10/1989 | Shimizu et al. |
| 4,892,674 | A | * | 1/1990 | Ho et al. ........................ 252/189 |
| 5,602,279 | A | | 2/1997 | Thaler et al. |
| 5,749,941 | A | * | 5/1998 | Jansen et al. ....................... 95/44 |
| 6,127,362 | A | | 10/2000 | Cignarella et al. |
| 6,436,174 | B1 | | 8/2002 | Grossmann et al. |

FOREIGN PATENT DOCUMENTS

| | | |
|---|---|---|
| GB | 2017524 | 10/1979 |
| WO | 03095071 A1 | 11/2003 |

* cited by examiner

*Primary Examiner* — Duane Smith
*Assistant Examiner* — Cabrena Hall
(74) *Attorney, Agent, or Firm* — Glenn T. Barrett; Malcolm D. Keen

(57) ABSTRACT

An acid gas absorbent comprising a metal sulfonate, phosphonate or carboxylate of a hindered amine and a process for the selective removal Of H2S as well as other acidic components such as carbon disulfide, carbonyl sulfide and oxygen and sulfur derivatives of C1 to C4 hydrocarbons from mixtures containing such acidic components and CO2 using said absorbent.

6 Claims, 1 Drawing Sheet

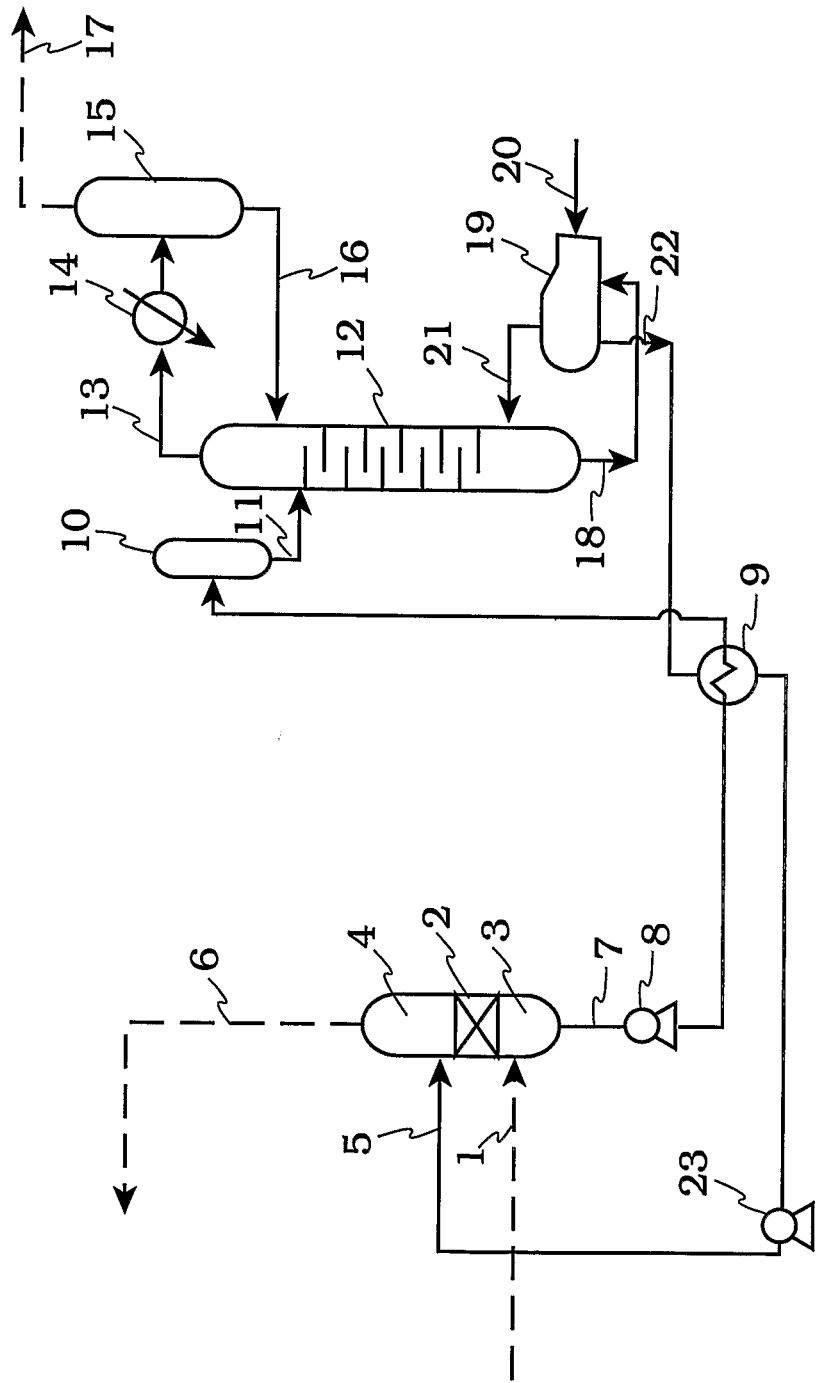

ABSORBENT COMPOSITION CONTAINING MOLECULES WITH A HINDERED AMINE AND A METAL SULFONATE, PHOSPHONATE OR CARBOXYLATE STRUCTURE FOR ACID GAS SCRUBBING PROCESS

BACKGROUND OF THE INVENTION

1. Field of the Invention

The present invention relates to an absorbent composition and to a process for the selective absorption of $H_2S$ from an $H_2S$ and other acidic components containing mixture using the absorbent composition.

2. Description of the Related Art

It is well known in the art to treat gases and liquids, such as mixtures containing acidic gases including $CO_2$, $H_2S$, $CS_2$, HCN, COS and oxygen and sulfur derivatives of $C_1$ to $C_4$ hydrocarbons with amine solutions to remove these acidic gases. The amine usually contacts the acidic gases and the liquids as an aqueous solution containing the amine in an absorber tower with the aqueous amine solution contacting the acidic fluid countercurrently.

The treatment of acid gas mixtures containing, inter alia, $CO_2$ and $H_2S$ with amine solutions typically results in the simultaneous removal of substantial amounts of both the $CO_2$ and $H_2S$. For example, in one such process generally referred to as the "aqueous amine process", relatively concentrated amine solutions are employed. A recent improvement of this process involves the use of sterically hindered amines as described in U.S. Pat. No. 4,112,052, to obtain nearly complete removal of acid gases such as $CO_2$ and $H_2S$. This type of process may be used where the partial pressures of the $CO_2$ and related gases are low. Another process often used for specialized applications where the partial pressure of $CO_2$ is extremely high and/or where many acid gases are present, e.g., $H_2S$, COS, $CH_3SH$ and $CS_2$ involves the use of an amine in combination with a physical absorbent, generally referred to as the "nonaqueous solvent process". An improvement on this process involves the use of sterically hindered amines and organic solvents as the physical absorbent such as described in U.S. Pat. No. 4,112,051.

It is often desirable, however, to treat acid gas mixtures containing both $CO_2$ and $H_2S$ so as to remove the $H_2S$ selectively from the mixture, thereby minimizing removal of the $CO_2$. Selective removal of $H_2S$ results in a relatively high $H_2S/CO_2$ ratio in the separated acid gas which simplifies the conversion of $H_2S$ to elemental sulfur using the Claus process.

The typical reactions of aqueous secondary and tertiary amines with $CO_2$ and $H_2S$ can be represented as follows:

$$H_2S + R_3N \rightleftarrows R_3NH^+ + SH^- \quad (1)$$

$$H_2S + R_2NH \rightleftarrows R_2NH_2^+ + SH^- \quad (2)$$

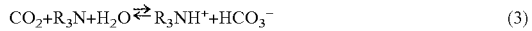
$$CO_2 + R_3N + H_2O \rightleftarrows R_3NH^+ + HCO_3^- \quad (3)$$

$$CO_2 + 2R_2NH \rightleftarrows R_2NH_2^+ + R_2NCOO^- \quad (4)$$

$$RNH_2 + CO_2 \rightleftarrows RN^+H_2CO_2^- \quad (5)$$

$$RN^+H_2CO_2 + RNH_2 \rightleftarrows RNHCO_2^- RNH_3^+ \quad (6)$$

wherein each R is an organic radical which may be the same or different and may be substituted with an hydroxy group. The above reactions are reversible, and the partial pressures of both $CO_2$ and $H_2S$ are thus important in determining the degree to which the above reactions occur.

While selective $H_2S$ removal is applicable to a number of gas treating operations including treatment of hydrocarbon gases from shale pyrolysis, refinery gas and natural gas having a low $H_2S/CO_2$ ratio, it is particularly desirable in the treatment of gases wherein the partial pressure of $H_2S$ is relatively low compared to that of $CO_2$ because the capacity of an amine to absorb $H_2S$ from the latter type gases is very low. Examples of gases with relatively low partial pressures of $H_2S$ include synthetic gases made by coal gasification, sulfur plant tail gas and low-Joule fuel gases encountered in refineries where heavy residual oil is being thermally converted to lower molecular weight liquids and gases.

Although it is known that solutions of primary and secondary amines such as monoethanolamine (MEA), diethanolamine (DEA), dipropanolamine (DPA), and hydroxyethoxyethylamine (DGA) absorb both $H_2S$ and $CO_2$ gas, they have not proven especially satisfactory for preferential absorption of $H_2S$ to the exclusion of $CO_2$ because the amines undergo a facile reaction with $CO_2$ to form carbamates as shown in Equations 5 and 6.

Diisopropanolamine (DIPA) is relatively unique among secondary amino alcohols in that it has been used industrially, alone or with a physical solvent such as sulfolane, for selective removal of $H_2S$ from gases containing $H_2S$ and $CO_2$, but contact times must be kept relatively short to take advantage of the faster reaction of $H_2S$ with the amine compared to the rate of $CO_2$ reaction shown in Equations 2 and 4 hereinabove.

In 1950, Frazier and Kohl, Ind. and Eng. Chem., 42, 2288 (1950) showed that the tertiary amine, methyldiethanolamine (MDEA), has a high degree of selectivity toward $H_2S$ absorption over $CO_2$. This greater selectivity was attributed to the relatively slow chemical reaction of $CO_2$ with tertiary amines as compared to the rapid chemical reaction of $H_2S$. The commercial usefulness of MDEA, however, is limited because of its restricted capacity for $H_2S$ loading and its limited ability to reduce the $H_2S$ content to the level at low pressures which is necessary for treating, for example, synthetic gases made by coal gasification.

Recently, U.K. Patent Publication No. 2,017,524A to Shell disclosed that aqueous solutions of dialkylmonoalkanolamines, and particularly diethyl-monoethanolamine (DEAE), have higher selectivity and capacity for $H_2S$ removal at higher loading levels than MDEA solutions. Nevertheless, even DEAE is not very effective for the low $H_2S$ loading frequency encountered in the industry. Also, DEAE has a boiling point of 161° C., and as such, it is characterized as being a low-boiling, relatively highly volatile amino alcohol. Such high volatilities under most gas scrubbing conditions result in large material losses with consequent losses in economic advantages.

U.S. Pat. Nos. 4,405,581; 4,405,583 and 4,405,585 disclose the use of severely sterically hindered amine compounds for the selective removal of $H_2S$ in the presence of $CO_2$. Compared to aqueous methyldiethanolamine (MDEA) severely sterically hindered amines lead to much higher selectivity at high $H_2S$ loadings.

U.S. Pat. No. 4,112,052 is directed to a process for removing $CO_2$ from acid gases using an aqueous amine scrubbing solution. The amines used are sterically hindered amines containing at least one secondary amine group attached to either a secondary or tertiary carbon atom or a primary amino group attached to a tertiary carbon atom. The amines are selected to be at least partially soluble in the solvent used, i.e., water.

U.S. Pat. No. 4,376,102 discloses that acidic gases containing $CO_2$ are removed from normally gaseous mixtures by absorbing the $CO_2$ from the gaseous mixture using an aqueous solution comprising a basic alkali metal salt or hydroxide which contains (1) at least one diaminoalcohol of the formula

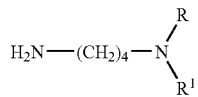

wherein R and R¹ are each independently a $C_1$-$C_6$ alkyl group and either R or R¹ or both R and R¹ have a pendent hydroxyl group and (2) an amino acid. The basic alkali metal salt or hydroxide are selected from the group consisting of alkali metal bicarbonates, carbonates, hydroxides, borates, phosphates and their mixtures. See also U.S. Pat. Nos. 4,376,101; 4,581,209; 4,217,238.

U.S. Pat. No. 4,525,294 is directed to amino acid mixtures, their alkali metal salts and processes for their preparation. The process involves the reductive condensation of glycine or alanine and their alkali metal salts with a ketone in the presence of a reductant such as hydrogen and a catalytically effective amount of an hydrogenation catalyst. Thus, a reaction as follows is disclosed:

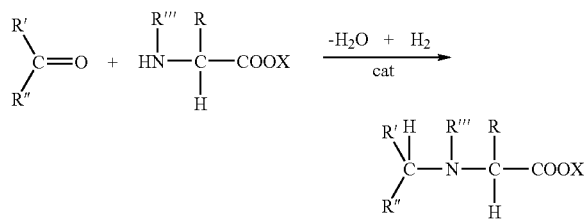

wherein R is hydrogen or methyl, X is hydrogen or an alkali metal such as sodium or potassium, R' and R" are selected from the group consisting of:
a) substituted or unsubstituted linear or branched allyl radicals having one to 20 carbons; or
b) substituted or unsubstituted alkylene radicals each having three to six carbon atoms and combined to form a cyclic ring;
c) substituted or unsubstituted cycloalkyl radicals having from four to eight ring carbon atoms;
d) substituted or unsubstituted hydroxyl alkyl radicals, linear or branched, having one to 20 carbon atoms; or
e) substituted or unsubstituted arylalkyl radicals having from seven to 20 carbon atoms;
and R''' is hydrogen or a substituted or unsubstituted linear alkyl radical having from 1 to 20 carbon atoms, or mixtures of hydrogen and such alkyl radicals.

U.S. Pat. No. 4,759,866 discloses primary sterically hindered amino acids of the formula:

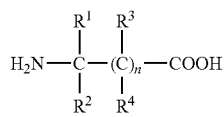

wherein $R^1$ and $R^2$ are independently selected from $CH_3$, $C_2H_5$ and $C_3H_7$, and $R^3$ and $R^4$ are independently hydrogen and $CH_3$ and n is zero, 2 or 3, for use as promoters for alkali metal salts in acid gas scrubbing.

U.S. Pat. No. 5,602,279 is directed to a gas treating composition prepared by reacting 2-amino-2-methyl-1-propanol with KOH, diluting with water and adding $K_2CO_3$ and a vanadium corrosion inhibitor. The acid gas scrubbing solution contains

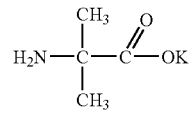

U.S. Pat. No. 4,618,481 is directed to an absorbent composition comprising a severely hindered amino compound and an amine salt for the absorption of $H_2S$ from gaseous mixtures. The severely sterically hindered amino compound can be a secondary amino ether alcohol, a disecondary amino ether, and mixtures thereof. The amine salt can be the reaction product of the aforesaid severely sterically hindered amino compound, a tertiary amino compound such as tertiary alkanolamines, triethanol amines, and mixtures thereof and a strong acid, or a thermally decomposable salt of a strong acid, i.e., ammonium salt or a component capable of forming a strong acid and mixtures thereof. Suitable strong acids include inorganic acids such as sulfuric acid, sulfurous acid, phosphoric acid, phosphorous acid, pyrophosphoric acid, an organic acid such as acetic acid, formic acid, adipic acid, benzoic acid, etc. Suitable salts of these acids include the ammonium salts, for example ammonium sulfate, ammonium sulfite, ammonium phosphate and mixtures thereof. Preferably ammonium sulfate (a salt) or $SO_2$ (a precursor of an acid) is used as reactant with the amine. Suitable amine salts are those that are non-volatile at conditions used to regenerate the absorbent composition.

U.S. Pat. No. 4,892,674 is directed to an absorbent composition comprising an alkaline absorbent solution containing a non-hindered amine and an additive of a severely-hindered amine salt and/or a severely-hindered aminoacid and to the use of the absorbent for the selective removal of $H_2S$ from gaseous streams. The amine salt is the reaction product of an alkaline severely hindered amino compound and a strong acid or a thermally decomposable salt of a strong acid, i.e., ammonium salt. Suitable strong acids include inorganic acids such as sulfuric acid, sulfurous acid, phosphoric acid, phosphorous acid, pyrophosphoric acid; organic acids such as acetic acid, formic acid, adipic acid, benzoic acid, etc. Suitable salts include the ammonium salts, for example, ammonium sulfate, ammonium sulfite, ammonium phosphate and mixtures thereof.

DESCRIPTION OF THE FIGURE

FIG. 1 is a diagrammatic flow sheet illustrating an absorption regeneration unit for the selective removal of $H_2S$ from gaseous streams containing $H_2S$ and $CO_2$.

SUMMARY OF THE INVENTION

The present invention is directed to an absorbent comprising a metal sulfonate, metal phosphonate or metal carboxylate of hindered amines and to a method for removing $H_2S$ from gaseous mixtures containing $H_2S$ using said absorbents.

DETAILED DESCRIPTION OF THE INVENTION

A composition for the selective absorption of normally gaseous acidic components, particularly $H_2S$, from mixtures containing gaseous acidic components including $CO_2$ and gaseous non-acidic components comprises a metal sulfonate, metal phosphonate, metal phosphate, metal sulfamate, metal phosphoramidate or metal carboxylate of a hindered secondary or tertiary amine wherein (i) the metal sulfonate, sulfamate, phosphonate, phosphate or phosphoramidate is attached to the amine nitrogen through a group containing at least one chain carbon, preferably 1 to 4 chain carbons, more preferably an alkylene group of 2 to 4 chain carbons, (ii) the metal carboxylate is attached to the amine nitrogen through an alkylene group containing 2 or more chain carbons.

The absorbents are generally represented by the following formulae:

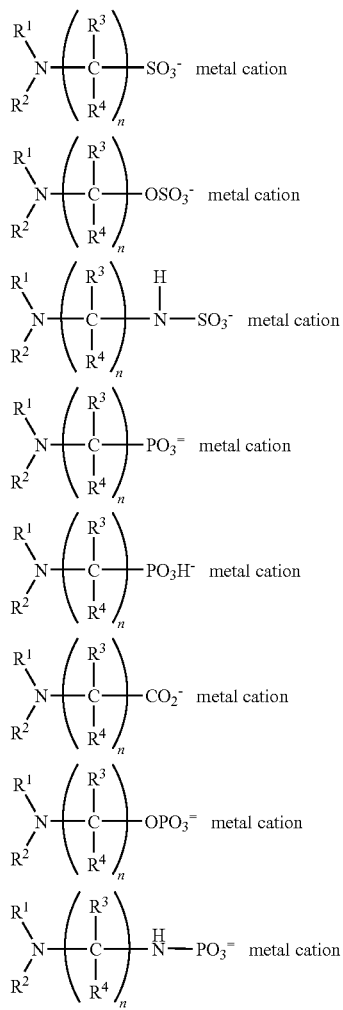

wherein $R^1$, $R^2$, $R^3$ and $R^4$ are the same or different and selected from H, $C_1$-$C_9$ substituted or unsubstituted straight or $C_3$-$C_9$ substituted or unsubstituted branched chain alkyl, $C_3$-$C_9$ cycloalkyl, $C_6$-$C_9$ aryl, alkylaryl, arylalkyl, $C_2$-$C_9$ straight or branched hydroxyalkyl, cycloalkyl and mixtures thereof provided both $R^1$ and $R^2$ are not hydrogen, and wherein when n is 2 or more, $R^3$ and $R^4$ on adjacent carbon or on carbons separated by one or more carbons can be a cycloalkyl or aryl ring and wherein when substituted the substituents are heteroatom containing substituents, preferably

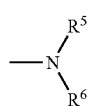

group wherein $R^5$ and $R^6$ are the same or different and selected from H, $C_1$-$C_9$ straight or $C_3$-$C_9$ branched chain alkyl, $C_3$-$C_9$ cycloalkyl, $C_6$-$C_9$ aryl, alkylaryl, arylalkyl, $C_2$-$C_9$ straight or branched chain hydroxyalkyl, cycloalkyl and mixtures thereof, provided $R^5$ and $R^6$ are not both H, and further wherein, optionally when $R^1$ is H, and n is 2 or more, $R^2$ and $R^3$ or $R^4$ on the carbon at least one carbon removed from the aminic nitrogen can form a ring, n is an integer of 1 or more, preferably 1 to 4, more preferably 2 to 4, and wherein when n is at least 2 the absorbent can be a metal carboxylate of the amine, metal cation is one or more monovalent, divalent or trivalent metal cation sufficient to satisfy the valence requirements of the anion or anion cluster, preferably magnesium, barium, aluminum, iron, sodium, lithium, potassium, calcium, nickel, cobalt. Salts formed from divalent cations can be half- or full-salts. Salts formed from trivalent cations can be one third, two third or full salts. By anion cluster is meant 2 or more anions the valence requirements of which are satisfied by, e.g., a single divalent or trivalent metal cation.

Preferably $R^1$ and $R^2$ are the same or different and are selected from H, $C_4$-$C_6$ substituted or unsubstituted straight or branched chain alkyl, cyclic alkyl, $C_6$-$C_7$ aryl, alkylaryl, arylalkyl $C_4$-$C_6$ straight or branched chain hydroxy alkyl, cycloalkyl and mixtures thereof, more preferably $C_4$-$C_6$ straight or branched chain alkyl, most preferably tertiary-butyl, provided both $R^1$ and $R^2$ are not hydrogen.

Examples of preferred materials are of the formula:

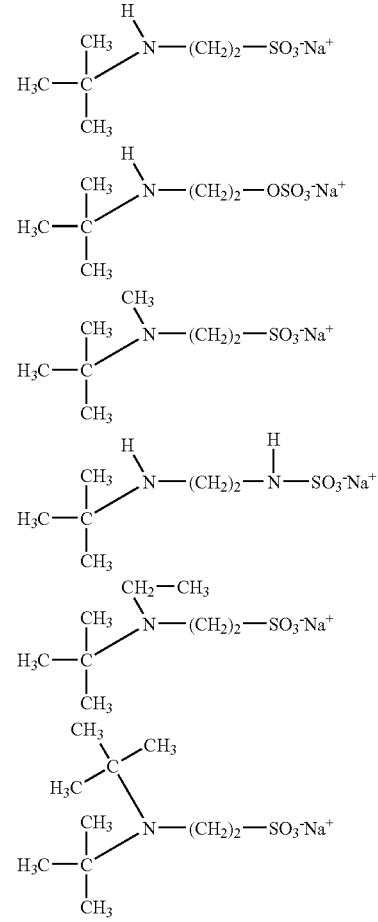

-continued

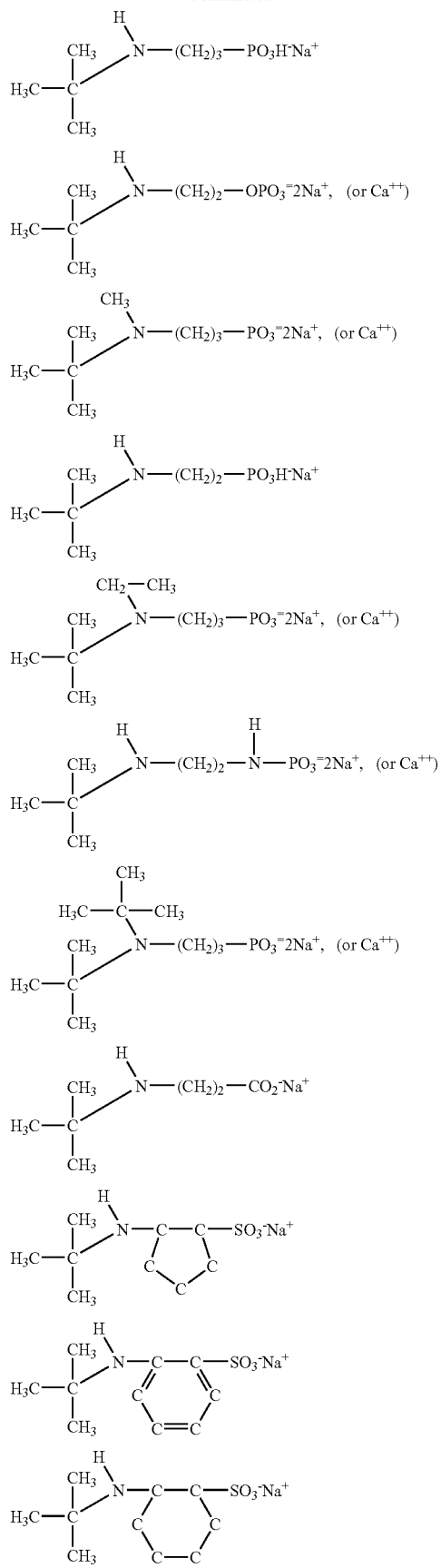

-continued

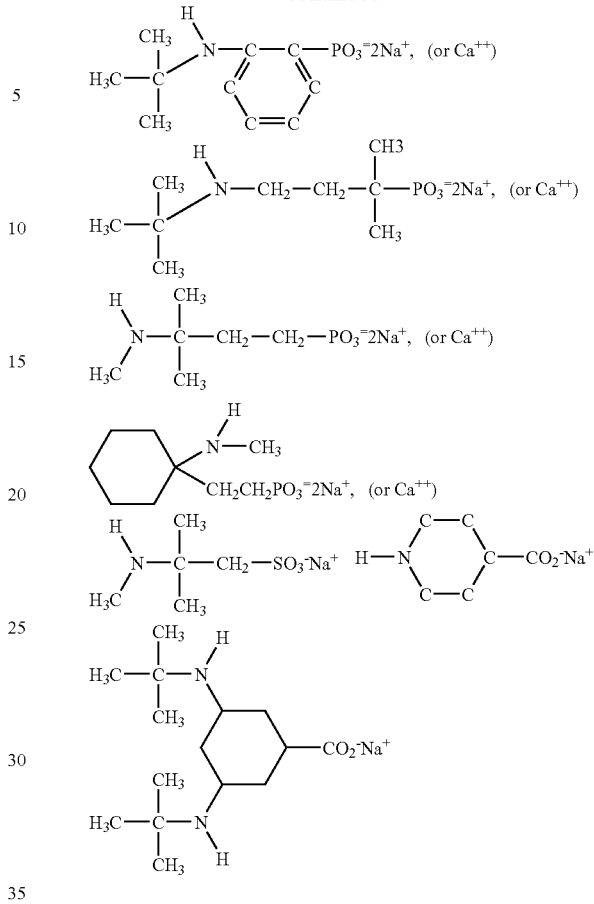

The absorbents described above exhibit high selectivity for $H_2S$ and other gaseous acidic component(s) removal from mixtures of said gaseous acidic components, non-acidic components, and $CO_2$ and retain their high selectivity and loading capacity even after regeneration.

The absorbents especially are utilized for the selective absorption of gaseous acid components, e.g., $H_2S$ from a normally gaseous mixture containing gaseous acidic components, e.g., $H_2S$, and non-acidic components and $CO_2$ comprising:

(a) contacting said normally gaseous mixture with an absorbent solution characterized as capable of selectively absorbing one or more gaseous acidic components, e.g., $H_2S$ from said mixture;

(b) regenerating, at least partially, said absorbent solution containing absorbent gaseous acid components, e.g., $H_2S$; and (c) recycling the regenerated solution for the selective absorption of one or more gaseous acidic components, e.g., $H_2S$ by contacting as in step (a).

Preferably, the regenerating step is carried out by heating and stripping and more preferably heating and stripping with steam.

The term "absorbent solution" as used herein includes but is not limited to solutions wherein the amino compound is dissolved in a solvent selected from water or a physical absorbent or mixtures thereof. Solvents which are physical absorbents (as opposed to the amino compounds which are chemical absorbents) are described, for example, in U.S. Pat. No. 4,112,051, the entire disclosure of which is incorporated herein by reference, and include, e.g., aliphatic acid amides, N-alkylated pyrrolidones, sulfones, sulfoxides, glycols and the mono- and diethers thereof. The preferred physical absorbents herein are sulfones, and most particularly, sulfolane. The preferred liquid medium comprises water.

The absorbent solution ordinarily has a concentration of amino compound of about 0.1 to 6 moles per liter of the total solution, and preferably 1 to 4 moles per liter, depending primarily on the specific amino compound employed and the solvent system utilized. If the solvent system is a mixture of water and a physical absorbent, the typical effective amount of the physical absorbent employed may vary from 0.1 to 5 moles per liter of total solution, and preferably from 0.5 to 3 moles per liter, depending mainly on the type of amino compound being utilized. The dependence of the concentration of amino compound on the particular compound employed is significant because increasing the concentration of amino compound may reduce the basicity of the absorbent solution, thereby adversely affecting its selectivity for $H_2S$ removal, particularly if the amino compound has a specific aqueous solubility limit which will determine maximum concentration levels within the range given above. It is important, therefore, that the proper concentration level appropriate for each particular amino compound be maintained to insure satisfactory results.

The solution of this invention may include a variety of additives typically employed in selective gas removal processes, e.g., antifoaming agents, antioxidants, corrosion inhibitors, and the like. The amount of these additives will typically be in the range that they are effective, i.e., an effective amount.

Also, the amino compounds described herein may be admixed with other amino compounds as a blend. The ratio of the respective amino compounds may vary widely, for example, from 1 to 99 wt % of the amino compounds described herein.

Three characteristics which are of ultimate importance in determining the effectiveness of the amino compounds herein for $H_2S$ removal are "selectivity", "loading" and "capacity". The term "selectivity" as used throughout the specification is defined as the following mole ratio fraction:

$$\frac{\text{(moles of } H_2S/\text{moles of } CO_2\text{) in liquid phase}}{\text{(moles of } H_2S/\text{moles of } CO_2\text{) in gaseous phase}}$$

The higher this fraction, the greater the selectivity of the absorbent solution for the $H_2S$ in the gas mixture.

By the term "loading" is meant the concentration of the $H_2S$ and $CO_2$ gases physically dissolved and chemically combined in the absorbent solution as expressed in moles of gas per moles of the amine. The best amino compounds are those which exhibit good selectivity up to a relatively high loading level. The amino compounds used in the practice of the present invention typically have a "selectivity" of not substantially less than 10 at a "loading" of 0.1 moles, preferably, a "selectivity" of not substantially less than 10 at a loading of 0.2 or more moles of $H_2S$ and $CO_2$ per moles of the amino compound.

"Capacity" is defined as the moles of $H_2S$ loaded in the absorbent solution at the end of the absorption step minus the moles of $H_2S$ loaded in the absorbent solution at the end of the desorption step. High capacity enables one to reduce the amount of amine solution to be circulated and use less heat or steam during regeneration.

The acid gas mixture herein necessarily includes $H_2S$, and may optionally include other gases such as $CO_2$, $N_2$, $CH_4$, $H_2$, CO, $H_2O$, COS, HCN, $C_2H_4$, $NH_3$, and the like. Often such gas mixtures are found in combustion gases, refinery gases, town gas, natural gas syn gas, water gas, propane, propylene, heavy hydrocarbon gases, etc. The absorbent solution herein is particularly effective when the gaseous mixture is a gas, obtained, for example, from shale oil retort, coal liquefaction or gasification, gasification of heavy oil with steam, air/steam or oxygen/steam, thermal conversion of heavy residual oil to lower molecular weight liquids and gases, e.g., fluid coker, Flexicoker, or delayed coker or in sulfur plant tail gas cleanup operations.

The absorption step of this invention generally involves contacting the normally gaseous stream with the absorbent solution in any suitable contacting vessel. In such processes, the normally gaseous mixture containing $H_2S$ and $CO_2$ from which the $H_2S$ as well as other acidic components such as carbon disulfide, carbonyl sulfide and oxygen and sulfur derivatives of $C_1$-$C_4$ hydrocarbon can be selectively removed may be brought into intimate contact with the absorbent solution using conventional means, such as a tower or vessel packed with, for example, rings or with sieve plates, or a bubble reactor. Other acidic gaseous components will also be removed.

In a typical mode of practicing the invention, the absorption step is conducted by feeding the normally gaseous mixture into the lower portion of the absorption tower while fresh absorbent solution is fed into the upper region of the tower. The gaseous mixture, freed largely from the $H_2S$, emerges from the upper portion of the tower, and the loaded absorbent solution, which contains the selectively absorbed $H_2S$, leaves the tower near or at its bottom. Preferably, the inlet temperature of the absorbent solution during the absorption step is in the range of from about 20° C. to about 100° C., and more preferably from 30° C. to about 60° C. Pressures may vary widely; acceptable pressures are between 5 and 2000 psia, preferably 20 to 1500 psia, and most preferably 25 to 1000 psia in the absorber. The contacting takes place under conditions such that the $H_2S$ is selectively absorbed by the solution. The absorption conditions and apparatus are designed so as to minimize the residence time of the liquid in the absorber to reduce $CO_2$ pickup while at the same time maintaining sufficient residence time of gas mixture with liquid to absorb a maximum amount of the $H_2S$ gas. The amount of liquid required to be circulated to obtain a given degree of $H_2S$ removal will depend on the chemical structure and basicity of the amino compound and on the partial pressure of $H_2S$ in the feed gas. Gas mixtures with low partial pressures such as those encountered in thermal conversion processes will require more liquid under the same absorption conditions than gases with higher partial pressures such as shale oil retort gases.

A typical procedure for the selective $H_2S$ removal phase of the process comprises selectively absorbing $H_2S$ via countercurrent contact of the gaseous mixture containing $H_2S$ and $CO_2$ with the solution of the amino compound in a column containing a plurality of trays at a low temperature, e.g., below 45° C., and at a gas velocity of at least about 0.3 ft/sec (based on "active" or aerated tray surface), depending on the operating pressure of gas, said tray column having fewer than 20 contacting trays, with, e.g., 4-16 trays being typically employed.

After contacting the normally gaseous mixture with the absorbent solution, which becomes saturated or partially saturated with $H_2S$, the solution may be at least partially regenerated so that it may be recycled back to the absorber. As with absorption, the regeneration may take place in a single liquid phase. Regeneration or desorption of the absorbent solution may be accomplished by conventional means such as pressure reduction of the solution or increase of temperature to a point at which the absorbed $H_2S$ flashes off, or bypassing the solution into a vessel of similar construction to that used in the absorption step, at the upper portion of the vessel, and passing an inert gas such as air or nitrogen or preferably steam upwardly through the vessel. The temperature of the solution during the regeneration step should be in the range from about 50° C. to about 170° C., and preferably from about 80° C. to 120° C., and the pressure of the solution on regeneration should range from about 0.5 to about 100 psia, preferably 1 to about 50 psia. The absorbent solution, after being cleansed of at least a portion of the $H_2S$ gas, may be recycled back to the absorbing vessel. Makeup absorbent may be added as needed.

In the preferred regeneration technique, the $H_2S$-rich solution is sent to the regenerator wherein the absorbed components are stripped by the steam which is generated by re-boiling the solution. Pressure in the flash drum and stripper is usually 1 to about 50 psia, preferably 15 to about 30 psia, and the temperature is typically in the range from about 50° C. to 170° C., preferably about 80° C. to 120° C. Stripper and flash temperatures will, of course, depend on stripper pressure, thus at about 15 to 30 psia stripper pressures, the temperature will be about 80° C. to about 120° C. during desorption. Heating of the solution to be regenerated may very suitably be effected by means of indirect heating with low-pressure steam. It is also possible, however, to use direct injection of steam.

In one embodiment for practicing the entire process herein, as illustrated in FIG. 1, the gas mixture to be purified is introduced through line 1 into the lower portion of a gas-liquid countercurrent contacting column 2, said contacting column having a lower section 3 and an upper section 4. The upper and lower sections may be segregated by one or a plurality of packed beds as desired. The absorbent solution as described above is introduced into the upper portion of the column through a pipe 5. The solution flowing to the bottom of the column encounters the gas flowing countercurrently and dissolves the $H_2S$ preferentially. The gas freed from most of the $H_2S$ exits through a pipe 6, for final use. The solution, containing mainly $H_2S$ and some $CO_2$, flow toward the bottom portion of the column, from which it is discharged through pipe 7. The solution is then pumped via optional pump 8 through an optional heat exchanger and cooler 9 disposed in pipe 7, which allows the hot solution from the regenerator 12 to exchange heat with the cooler solution from the absorber column 2 for energy conservation. The solution is entered via pipe 7 to a flash drum 10 equipped with a line (not shown) which vents to line 13 and then introduced by pipe 11 into the upper portion of the regenerator 12, which is equipped with several plates and effects the desorption of the $H_2S$ and $CO_2$ gases carried along in the solution. This acid gas is passed through a pipe 13 into a condenser 14 wherein cooling and condensation of water and amine solution from the gas occur. The gas then enters a separator 15 where further condensation is effected. The condensed solution is returned through pipe 16 to the upper portion of the regenerator 12. The gas remaining from the condensation, which contains $H_2S$ and some $CO_2$, is removed through pipe 17 for final disposal (e.g., to a vent or incinerator or to an apparatus which converts the $H_2S$ to sulfur, such as a Claus unit or a Stretford conversion unit (not shown).

The solution is liberated from most of the gas which it contains while flowing downward through the regenerator 12 and exits through pipe 18 at the bottom of the regenerator for transfer to a reboiler 19. Reboiler 19, equipped with an external source of heat (e.g., steam injected through pipe 20 and the condensate exits through a second pipe (not shown)), vaporizes a portion of this solution (mainly water) to drive further $H_2S$ therefrom. The $H_2S$ and steam driven off are returned via pipe 21 to the lower section of the regenerator 12 and exited through pipe 13 for entry into the condensation stages of gas treatment. The solution remaining in the reboiler 19 is drawn through pipe 22, cooled in heat exchanger 9, and introduced via the action of pump 23 (optional if pressure is sufficiently high) through pipe 5 into the absorber column 2.

Typically, a gaseous stream to be treated having a 1:10 mole ratio of $H_2S:CO_2$ from an apparatus for thermal conversion of heavy residual oil, or a Lurgi coal gas having a mole ratio of $H_2S:CO_2$ of less than 1:10 will yield an acid gas having a mole ratio of $H_2S:CO_2$ of about 1:1 after treatment by the process of the present invention. The process herein may be used in conjunction with another $H_2S$ selective removal process; however, it is preferred to carry out the process of this invention by itself, since the amino compounds are extremely effective by themselves in preferential absorption of $H_2S$.

Preparation of Test Samples

Preparation of sodium tert-butylaminomethylsulfonate

37% Formaldehyde solution (18 g, 0.22 mol) was added to a suspension of sodium bisulfite (22 g, 0.2 mol) in water (25 mL). To this mixture was added tert-butylamine (28 mL, 19.4 g, 0.26 mol) at such a rate that the temperature of the reaction mixture was not exceeding 30° C. When the addition was complete, a distillation apparatus was set and the mixture was stirred at 70-75° C. for 10 minutes (excess of tert-butylamine was distilled off) and cooled to 10-15° C. The formed precipitate was filtered, washed with methanol and dried at 20-25° C. to give sodium tert-butylaminomethylsulfonate (30 g, 80%), as white plates, decomposition without melting above 180-190° C. (smell of amine), $^1H$ NMR (DMSO-$d_6$) δ 1.02 (s, 9H), 3.32 (s, 2H); $^{13}C$ NMR δ 28.9, 49.9, 60.8.

Sodium 2-(tert-butylamino) ethylsulfonate tert-Butylamine (127 mL, 88 g, 1.2 mol) was added to a solution of sodium 2-hydroxyethylsulfonate (29.6 g, 0.2 mol) and disodium phosphate (1.1 g, 8 mmol) in water (50 mL). The mixture was stirred at 240-245° C. (6.5 MPa) in an autoclave for 3 hours. The mixture was then cooled to 50-60° C. and concentrated to 50 mL under normal pressure. After cooling to 10-15° C., the formed precipitate was filtered, washed with methanol and dried at 20-25° C., yield 10 g. The filtrate was concentrated under normal pressure to approximately 25-30 mL giving an additional 5.6 g of product. Total yield of sodium 2-(tert-butylamino)ethylsulfonate is 15.6 g, 38%, as white plates, decomposition 145-150° C. (become semi-fluid), $^1H$ NMR (DMSO-$d_6$) δ 1.00 (s, 9H), 2.56 (t, J=6.6 Hz, 2H), 2.72 (t, J=6.6 Hz, 2H); $^{13}C$ NMR δ 28.9, 38.6, 49.6, 52.2.

3-(tert-Butylamino)propylsulfonic acid

To a solution of 1,3-propanesultone (20 g, 0.164 g) in toluene (100 mL) was added tert-butylamine (90 mL, 62.1 g, 0.85 mol). The mixture was stirred under gentle reflux for 1 hour. The precipitate was filtered, washed with diethyl ether and dried at 20-25° C. Yield 3-(tert-butylamino)propylsulfonic acid 32 g (approximately 100%), as white microcrystals, mp above 280° C., $^1H$ NMR (D$_2$O) δ 1.33 (s, 9H), 2.07 (p, J=7.6 Hz, 2H), 2.99 (t, J=7.6 Hz, 2H), 3.15 (t, J=7.7 Hz, 2H); $^{13}C$ NMR δ 21.3, 24.3, 39.4, 47.4, 56.5.

Sodium 3-(tert-butylamino)propylsulfonate 3-(tert-Butylamino)propylsulfonic acid (18 g) was added to a solution of sodium hydroxide (3.69 g, 0.092 mol) in methanol (300 mL). The mixture was stirred till become clear. The solvent was removed and the solid residue was dried in vacuum to give sodium 3-(tert-butylamino)propylsulfonate (18.7 g), as white microcrystals, decomposition at 170° C., $^1$H NMR (D$_2$O) δ 1.08 (s, 9H), 1.80-1.90 (m, 2H), 2.64 (t, J=7.6 Hz, 2H), 2.91-2.96 (m, 2H); $^{13}$C NMR δ 24.4, 26.9, 39.8, 48.7, 49.6.

The preparation of disodium tert-butylaminomethylphosphonate

N-Methylene-tert-butylamine was prepared followed published procedure [U.S. Pat. No. 2,750,416] with some modifications as follows:

37% Aqueous formaldehyde (89 g of solution, 33 g, 1.1 mol) was added dropwise with stirring to tert-butylamine (73 g, 1 mol) over 20 minutes keeping the temperature below 20° C. (cooling on ice-bath). The reaction mixture was stirred for 30 minutes at 20-22° C., cooled to 5-10° C. and potassium hydroxide (30 g) was added portionwise with cooling at 15-20° C. The organic layer was separated and dried over potassium hydroxide pellets. The attempted purification by distillation gave unsatisfactory results due to trimerization of N-methylene-tert-butylamine at elevated temperature. The purification of the crude product was achieved by the distillation in the presence of catalytic p-toluenesulfonic acid (on 10 cm column, oil-bath 115-120° C.) to give pure N-methylene-tert-butylamine in 87% yield (74 g), bp 66-67° C. (lit. [U.S. Pat. No. 2,750,416] 64-65° C.); $^1$H NMR (CDCl$_3$) 1.20 (s, 9H), 7.26 (d, J=16.0 Hz, 1H), 7.41 (d, J=16.0 Hz, 1H).

Diethyl tert-butylaminomethylphosphonate

Diethyl phosphite (41.4 g, 0.3 mol) was added to N-methylene-tert-butylamine (25.6 g, 0.3 mol) under nitrogen atmosphere. Within 1-2 minutes the temperature of the mixture spontaneously rose to 60-70° C. The mixture was stirred at 80° C. for 30 minutes and then at 20-25° C. for 12 hours. The NMR test of the mixture showed pure diethyl tert-butylaminomethylphosphonate, as a colorless oil, $^1$H NMR (CDCl$_3$) δ 1.08 (s, 9H), 1.34 (t, J=7.0 Hz, 6H), 2.93 (d, J=15.1 Hz, 2H), 4.11-4.22 (m, 4H); $^{13}$C NMR δ 16.4 (d, J=5.7 Hz), 28.4, 38.6 (d, J=159.2 Hz), 50.8 (d, J=17.8 Hz), 62.1 (d, J=6.9 Hz). "Novel Synthesis of Aminomethyl Phosphoric Acid, Moedritzer, K., Synthesis in Inorganic and Metal-Organic Chemistry, 1972, 2, 317.

tert-Butylaminomethylphosphonic acid

The above crude ester (65 g) was added dropwise to concentrated hydrochloric acid (200 mL). The mixture was stirred at 90° C. for 20 hours. The mixture was concentrated in vacuum to solidifying and ethanol (300 mL) was added to the residue. The mixture was cooled to −5° C. for 30 minutes. The precipitate was filtered and washed with diethyl ether to give 44 g (90%) of crude acid (contaminated with adsorbed hydrogen chloride).

The crude acid was dissolved in boiling water (60 mL) followed by the addition of methanol (500 mL) and immediately propylene oxide (20 mL). The mixture was cooled to −5° C. for 1 hour, and the precipitate was filtered and washed with methanol and diethyl ether to give 40.5 g of tert-butylaminomethylphosphonic acid, white needles, mp 295° C. decomposition (Moedritzer, K., op cit) 289° C. decomposition); $^1$H NMR (D$_2$O) δ 1.31 (s, 9H), 3.03 (d, J=13.9 Hz, 2H); $^{13}$C NMR δ 23.9, 37.6 (d, J=137.4 Hz), 58.1 (d, J=7.4 Hz).

Disodium tert-butylaminomethylphosphonate tert-Butylaminomethylphosphonic acid (18.4 g, 0.11 mol) was added to sodium hydroxide (8.8 g, 0.22 mol) solution in methanol (100 mL). The mixture was stirred under reflux for 2 hours. The mixture was concentrated in vacuum until solidifying (approximately to ⅓ of volume) and diethyl ether was added (200 mL). The precipitate was filtered and washed with diethyl ether to give disodium tert-butylaminomethylphosphonate (20 g, 86%), white micro-crystals, decomposition 350-400° C.; $^1$H NMR (D$_2$O) δ 1.02 (s, 9H), 2.47 (d, J=15.0 Hz, 2H); $^{13}$C NMR δ 26.4, 40.1 (d, J=136.3 Hz), 50.6 (d, J=12.0 Hz).

Experimental Procedure

1. Absorption tests were carried out at 35° C. on 0.15 M aqueous solutions of absorbent using a gas mixture of nitrogen:carbon dioxide:hydrogen sulfide of 89:10:1 for 2 hours.
2. Desorption experiments were run at 85° C. in flowing nitrogen for 2 hours at the same flow rate as the test gas mixture.

The absorbents tested and the absorption results of both fresh absorbent and regenerated absorbent are presented in Table 1.

TABLE 1

| | Compound | Molecular weight | Selectivity | Loading (%) | Capacity (%) | Selectivity Reabsorption |
|---|---|---|---|---|---|---|
| 1 | TBA-CH$_2$—SO$_3$Na | 189.21 | 14.4 | 5.4 | 71 | 4.5 |
| 2 | TBA-(CH$_2$)$_2$—SO$_3$Na | 203.24 | 34.9 | 13.3 | 82 | 22.5 |
| 3 | TBA-(CH$_2$)$_3$—SO$_3$Na | 217.26 | 20.4 | 14.9 | 54 | 29.5 |
| 4 | TBA-(CH$_2$)$_3$—SO$_3$H | 196.29 | 1.2 | 0.2 | — | — |
| 5 | TBA-CH$_2$—PO$_3$H$_2$, Et$_3$N | 369.5 | — | — | — | — |
| 6 | TBA-(CH$_2$)—PO$_3^-$Na$_2^+$ | 314 | 103.8 | 17.8 | 22.6 | 92.41 |
| 7 | TBA-(CH$_2$)$_2$—PO$_3$H$_2$, Et$_3$N | 383.55 | 0.2 | 25.1 | — | — |
| 8 | TBA-(CH$_2$)$_2$—PO$_3^-$Na$_2^+$ | 328 | 107.2 | 14.2 | 52.2 | 81.8 |
| 9 | TBA-(CH$_2$)$_3$—PO$_3$H$_2$, Et$_3$N | 397.58 | 0.4 | 25.7 | — | — |
| 10 | TBA-(CH$_2$)$_3$—PO$_3^-$Na$_2^+$ | 342 | 59.9 | 14.5 | 29.8 | 47.8 |
| 11 | TBA-(CH$_2$)$_4$—PO$_3$H$_2$, Et$_3$N | 411.60 | 0.8 | — | — | — |
| 12 | TBA-(CH$_2$)$_4$—PO$_3^-$Na$_2^+$ | 356.08 | 67.2 | 15.6 | 63.5 | 78.6 |
| 13 | TBA-CH$_2$—CO$_2^-$Na$^+$ | 153.15 | 10.8 | 33.0 | 69.3 | 18.3 |
| 14 | TBA-(CH$_2$)$_3$—CO$_2^-$Na$^+$ | 181.21 | 19.3 | 30.8 | 49.3 | 16.8 |
| 15 | EETB | 161.24 | 15.4 | 16.3 | 60 | 13.3 |
| | (U.S. Pat. No. 4,405,585) | | 12.6 | 19.1 | 58 | 11.2 |
| | | | 15.6 | 16.7 | 64 | 21.5 |

Selectivity = (H$_2$S/CO$_2$) in solution/(H$_2$S/CO$_2$) in feed gas
Loading = Moles of H$_2$S/Moles of absorbent compound $$\text{Capacity} = \frac{\text{Moles of H}_2\text{S absorbed by absorbent solution/Moles of H}_2\text{S remaining after desorption from solution}}{\text{Moles of H}_2\text{S absorbed by absorbent solution}}$$

The invention claimed is:

1. An absorbent for the selective absorption of $H_2S$ from gaseous mixtures containing $H_2S$ and $CO_2$, said absorbent having the formula:

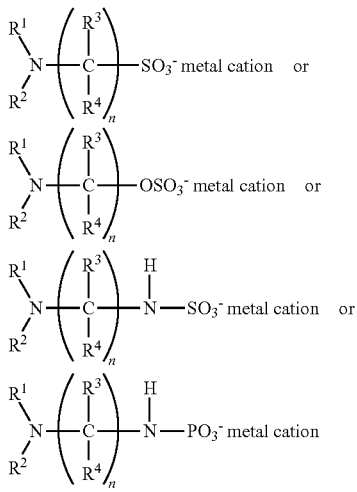

wherein $R^1$ is a tertiary $C_4$-$C_9$ alkyl group, $R^2$, $R^3$ and $R^4$ are the same or different and selected from hydrogen, $C_1$-$C_9$ substituted or unsubstituted alkyl $C_3$-$C_9$ substituted or unsubstituted branched chain alkyl, $C_3$-$C_9$ cycloalkyl, $C_6$-$C_9$ aryl, alkylaryl or arylalkyl, $C_2$-$C_9$ straight or branched hydroxyalkyl, hydroxy cycloalkyl wherein (i) when n is 2 or more, $R^3$ and $R^4$ on adjacent carbon or on carbons separated by one or more carbons can be a cycloalkyl or aryl ring, (ii) when substituted, the substituents are heteroatom containing substituents, (iii) n is an integer of 1 or more, and (iv) metal cation is a monovalent, divalent or trivalent metal cation sufficient to satisfy the valence requirements of the anion or anion cluster.

2. A process for the selective absorption of $H_2S$ from gaseous mixtures of $H_2S$, $CO_2$ and non-acidic comonents by contacting said mixture with an absorbent amino-containing solution comprising an absorbent having the formula:

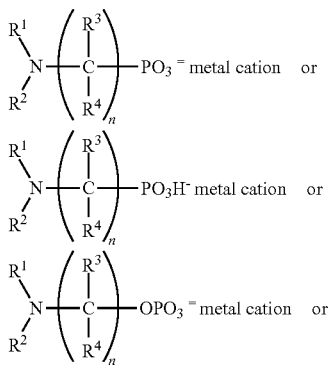

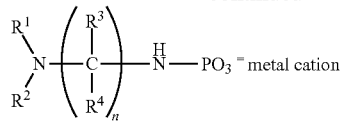

wherein $R^1$ is a tertiary $C_4$-$C_9$ alkyl group, $R^2$, $R^3$ and $R^4$ are the same or different and selected from hydrogen, $C_1$-$C_9$ substituted or unsubstituted alkyl $C_3$-$C_9$ substituted or unsubstituted branched chain alkyl, $C_3$-$C_9$ cycloalkyl, $C_6$-$C_9$ aryl, alkylaryl or arylalkyl, $C_2$-$C_9$ straight or branched hydroxyalkyl, hydroxy cycloalkyl wherein (i) when n is 2 or more, $R^3$ and $R^4$ on adjacent carbon or on carbons separated by one or more carbons can be a cycloalkyl or aryl ring, (ii) when substituted, the substituents are heteroatom containing substituents, (iii) n is an integer of 2 or more, and (iv) metal cation is one or more monovalent, divalent or trivalent metal cation sufficient to satisfy the valence requirement of the anion or anion cluster, under conditions whereby the $H_2S$ is selectively absorbed from said mixture.

3. The absorbent of claim 1 having the formula:

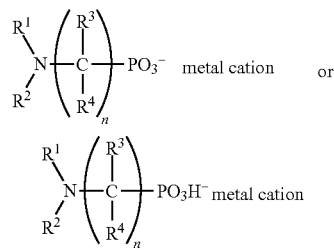

in which $R^1$ is a tertiary $C_4$-$C_9$ alkyl group, $R^2$, $R^3$ and $R^4$ are hydrogen, n is 1, 2, 3 or 4 and metal cation is Na.

4. The absorbent of claim 3 in which $R^1$ is tertiary butyl.

5. The process of claim 2 in which the absorbent comprises a compound of the formula:

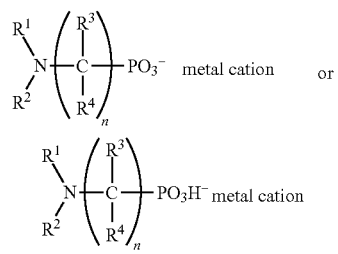

in which $R^1$ is a tertiary $C_4$-$C_9$ alkyl group, $R^2$, $R^3$ and $R^4$ are hydrogen, n is 1, 2, 3 or 4 and metal cation is Na.

6. The process of claim 5 in which $R^1$ is tertiary butyl.

* * * * *

UNITED STATES PATENT AND TRADEMARK OFFICE
CERTIFICATE OF CORRECTION

PATENT NO. : 8,480,795 B2
APPLICATION NO. : 11/989154
DATED : July 9, 2013
INVENTOR(S) : Siskin et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1245 days.

Signed and Sealed this
Eighth Day of September, 2015

Michelle K. Lee
*Director of the United States Patent and Trademark Office*